US009435776B2

(12) United States Patent
Li et al.

(10) Patent No.: US 9,435,776 B2
(45) **Date of Patent: *Sep. 6, 2016**

(54) IMMUNOSORBENT AND IMMUNOAFFINITY COLUMN FOR AFLATOXIN M1 NANOBODY AND PREPARATION METHOD THEREOF

(71) Applicant: OILCROPS RESEARCH INSTITUTE OF CHINESE ACADEMY OF AGRICULTURE SCIENCES, Wuhan, Hubei (CN)

(72) Inventors: Peiwu Li, Hubei (CN); Qi Zhang, Hubei (CN); Ting He, Hubei (CN); Zhaowei Zhang, Hubei (CN); Xiaoxia Ding, Hubei (CN)

(73) Assignee: OILCROPS RESEARCH INSTITUTE OF CHINESE ACADEMY OF AGRICULTURE SCIENCES, Wuhan, Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/667,378

(22) Filed: Mar. 24, 2015

(65) Prior Publication Data

US 2015/0276729 A1 Oct. 1, 2015

(30) Foreign Application Priority Data

Mar. 28, 2014 (CN) .......................... 2014 1 0121748

(51) Int. Cl.
| | |
|---|---|
| *G01N 33/543* | (2006.01) |
| *G01N 1/40* | (2006.01) |
| *G01N 30/02* | (2006.01) |
| *A61K 51/10* | (2006.01) |
| *B01J 20/281* | (2006.01) |
| *G01N 30/00* | (2006.01) |

(52) U.S. Cl.
CPC ........ *G01N 30/48* (2013.01); *G01N 33/54346* (2013.01); *G01N 2030/486* (2013.01)

(58) Field of Classification Search
CPC .. A61K 51/10; A61K 51/1009; G01N 33/53; G01N 2333/38; G01N 30/48; G01N 33/54346; G01N 33/543; G01N 2030/486; G01N 2030/482; G01N 30/02
See application file for complete search history.

(56) References Cited

PUBLICATIONS

Xiao Zhi-jun et al., "Development of a new high performance immunoaffinity micro-column for aflatoxin B1 purification in crain and oil", Chinese Journal of Oil Crop Sciences, 2006, 335-341, 28(3).
Sun Xing-Rong et al., "Preparation of Immunoaffinity Column for Anti-AFM1", Modern Food Science and Technology, 2011, 306-309, vol. 27, No. 3.

*Primary Examiner* — Shafiqul Haq
*Assistant Examiner* — Carmencita M Belei
(74) *Attorney, Agent, or Firm* — Tim Tingkang Xia, Esq.; Locke Lord LLP

(57) ABSTRACT

An aflatoxin M1 nanobody, an immunosorbent and an immunoaffinity column. The aflatoxin M1 nanobody 2014AFM-G2 has the amino acid sequence of SEQ ID NO:7, is encoded by the nucleic acid sequence of SEQ ID NO:8, has a 50% inhibiting concentration $IC_{50}$ to aflatoxin M1 of 0.208 ng/mL, and has cross reaction rates with aflatoxins B1, B2, G1, and G2 of 9.43%, 5.93%, 4.87% and 6.17%, respectively. The immunosorbent includes a solid phase carrier and aflatoxin M1 nanobody 2014AFM-G2 coupled with the solid phase carrier. The immunoaffinity column is loaded with the aflatoxin M1 nanobody immunosorbent. It can be used for purifying and concentrating an extracting solution of a sample before loading to a machine for detection and the immunoaffinity column can be used repeatedly for many times.

6 Claims, No Drawings

IMMUNOSORBENT AND IMMUNOAFFINITY COLUMN FOR AFLATOXIN M1 NANOBODY AND PREPARATION METHOD THEREOF

CROSS-REFERENCE TO RELATED APPLICATION

This non-provisional application claims priority under 35 U.S.C. §119(a) on Patent Application No. 201410121748.7 filed in P.R. China on Mar. 28, 2014, the entire contents of which are hereby incorporated by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to an immunosorbent and immunoaffinity column for aflatoxin M1 nanobody and a preparation method thereof.

BACKGROUND OF THE INVENTION

Aflatoxins are a group of highly toxic metabolites mainly produced by *Aspergillus flavus* and *Aspergillus parasiticus*. Aflatoxins are one category of most powerful carcinogenic substances ever discovered. 20 kinds of aflatoxins have now been found, mainly including aflatoxin B1 ($AFB_1$), B2 ($AFB_2$), G1 ($AFG_1$), G2 ($AFG_2$) and M1 ($AFM_1$), etc. Among them, $AFB_1$ is the most toxic. Aflatoxin M1 ($AFM_1$) is a hydroxylated metabolite of AFB1. When mammals ingest a feed contaminated by AFB1, AFB1 would be hydroxylated in vivo and secreted into milk. In general, after the animals ingesting a food contaminated by AFB1, the discharge amount of $AFM_1$ is 1%-3% of the intake amount of AFB1. A large number of researchers have conducted deep research on the toxicity and carcinogenicity of $AFM_1$, and the research results motivated International Agency for Research on Cancer to change the carcinogenic rank of $AFM_1$ from the category II carcinogenic substance to the category I carcinogenic substance. $AFM_1$ is stable in property and almost completely impossible to be destroyed even if it is subjected to pasteurization. $AFM_1$ is present in many dairy products. Since dairy products are the main source of infant foods, the problems about the $AFM_1$ contamination have attracted worldwide attention and the amount of $AFM_1$ is strictly limited in those dairy products. China belongs to heavily contaminated areas of aflatoxins, and therefore it is of important significance to intensify the detection especially the rapid detection of $AFM_1$ in milk and dairy products to timely understand and grasp the health information about the milk and dairy products for ensuring the safety of food consumption in China.

The existing detection methods for aflatoxins include thin-layer chromatography, precision instrument analysis method and immunological analysis method. Among them, thin-layer chromatography is the most common detection method used for aflatoxins very early. Thin-layer chromatography does not need special instruments and equipment and can be carried out in ordinary laboratories, but it has the problems of large reagent consumption, tedious operation, severe interference by other components, poor accuracy, incapability of accurate quantification, great harm to experimenters and surrounding environment, and inapplicability to in-field rapid detection. The precision instrument analysis method mainly includes fluorospectrophotometry and high performance liquid chromatography. These methods have high sensitivity and good accuracy, but they require high purity of aflatoxin samples, require tedious traditional sample pretreatment processes such as liquid-liquid extraction, solid phase extraction, solid-phase microextraction, and have low specificities. Therefore, the establishment of rapid and effective sample pretreatment techniques has become the principle and bottleneck problem in the detection and analysis of aflatoxins. An immunoaffinity column is a novel highly efficient sample pretreatment means, which is based on reversible specific binding between antigens and antibodies to realize the enrichment and purification of the target substance in a complex sample. The combination of the immunoaffinity column with liquid phase chromatographic analysis, fluorescence tachometer and the ELISA method can be widely used in the detection of aflatoxins in agricultural products and foods.

Currently, the preparation of immunoaffinity column for aflatoxins is implemented by coupling traditional antibodies (polyclonal antibodies or monoclonal antibodies) with an agarose gel or silica gel microspheres. Since the activities of the traditional antibodies degrade rapidly during use, it is a technical problem that the repeatable times for use of the existing immunoaffinity column on the market are relatively less. A nanobody is a heavy chain antibody naturally found in camelidae. Comparing with traditional antibody, the nanobody has advantages such as good stability, tolerance to high temperature, tolerance to acids and bases, and tolerance to organic reagents, and can be used in preparing an immunoaffinity column to prolong the shelf life of the immunoaffinity column. Further, nanobody can be produced through genetic engineering means, and thus the production cost of nanobody is low, and the production of nanobody is easy. Therefore, nanobody is more advantageous than conventional antibody in the preparation of an immunoaffinity column. Currently, there is still no report related to the immunosorbent and immunoaffinity column for aflatoxin nanobodies.

SUMMARY OF THE INVENTION

In one aspect, the present invention relates to an aflatoxin M1 nanobody immunosorbent, an immunoaffinity column using the immunosorbent, and the preparation method of the immunoaffinity column.

In one embodiment, an aflatoxin M1 nanobody immunosorbent includes a solid phase carrier and an aflatoxin nanobody coupled to the solid phase carrier. The aflatoxin nanobody is aflatoxin M1 nanobody 2014AFM-G2. The aflatoxin M1 nanobody 2014AFM-G2 has the amino acid sequence of SEQ ID NO:7, and is encoded by the gene sequence of SEQ ID NO:8.

In one embodiment, the amino acid sequences of three complementary determining regions of the aflatoxin M1 nanobody 2014AFM-G2 are: the amino acid sequence of CDR1 as shown in SEQ ID NO:1, the amino acid sequence of CDR2 as shown in SEQ ID NO:2, the amino acid sequence of CDR3 as shown in SEQ ID NO:3, respectively. In one embodiment, the encoding gene sequences of the three complementary determining regions are: the encoding gene sequence of CDR1 as shown in SEQ ID NO:4, the encoding gene sequence of CDR2 as shown in SEQ ID NO:5, and the encoding gene sequence of CDR3 as shown in SEQ ID NO:6, respectively.

In one embodiment, the solid phase carrier is an agarose gel or silica gel microspheres.

In one embodiment, an aflatoxin M1 nanobody immunoaffinity column is loaded with the above-mentioned aflatoxin M1 nanobody immunosorbent.

In one embodiment, a preparation method of the aflatoxin M1 nanobody immunoaffinity column includes: firstly filling a solid-phase extraction tube with an aflatoxin M1 nanobody immunoaffinity adsorbent, then adding pH6.0, 0.01 M phosphate buffer and allowing precipitation naturally, further washing with pH6.0, 0.01 M phosphate buffer, and storing in pH6.0, 0.01 M phosphate buffer containing 0.02 wt % sodium azide to obtain the aflatoxin M1 nanobody immunoaffinity column. In one embodiment, when the silica gel microspheres are chosen as the solid phase carrier in the aflatoxin M1 nanobody immunosorbent, the preparation method thereof includes: weighing 1-5 g silica gel microspheres, alternately rinsing with purified water and pH6.0 phosphate buffer, then measuring 5-25 mL, pH6.0 phosphate buffer to dissolve the silica gel microspheres, stirring and suspending the silica gel microspheres to obtain a suspension of silica gel microspheres; dissolving 2-10 mg aflatoxin M1 nanobody 2014AFM-G2 in 1-5 mL, pH6.0 phosphate buffer, and then adding dropwise to the suspension of silica gel microspheres; and finally weighing 70-350 mg carbodiimide, rapidly adding to the suspension of silica gel microspheres, and allowing reaction under stirring at 4° C. for 18-22 h to obtain the aflatoxin M1 nanobody immunosorbent using silica gel microspheres as the solid phase carrier. In one embodiment, when the agarose gel is chosen as the solid phase carrier in the aflatoxin M1 nanobody immunosorbent, the preparation method thereof includes: weighing 0.3-1 g agarose, repeatedly rinsing with 1 mM HCl solution, dissolving agarose in 5-15 mL coupling buffer, then adding 0.6-2 mg aflatoxin M1 nanobody 2014AFM-G2, stirring at room temperature for reaction for 1-2 h to obtain an agarose gel solution, filtering out the antibody solution in the agarose gel solution which is not coupled with the agarose gel, rinsing the agarose gel with the coupling buffer, then adding 0.1 M, pH8.0 Tris-HCl buffer, allowing reaction at room temperature for 2 h, and then alternately rinsing the agarose gel with 0.1 M, pH8.0 Tris-HCl buffer and 0.1 M, pH4.0 Tris-HCl buffer to obtain the aflatoxin M1 nanobody immunoaffinity adsorbent using agarose gel as the solid phase carrier. The coupling buffer is 0.1 M $NaCO_3$, 0.5 M NaCl, pH8.3.

In one embodiment, an application of the above-mentioned aflatoxin M1 nanobody immunoaffinity column includes using the aflatoxin M1 nanobody immunoaffinity column to purify and concentrate an extracting solution of a sample before loading to a machine. The specific operations are: firstly rinsing the prepared aflatoxin M1 nanobody immunoaffinity column with purified water, then adding the extracting solution of the sample, finally rinsing with purified water, after the liquid drain completely, eluting with methanol and collecting the eluate. The eluate is the purified and concentrated extracting solution of the sample, which can be used directly for loading to a machine for detection.

Certain embodiments of the present invention, among other things, have the following beneficial advantages:

(1) The aflatoxin M1 nanobody 2014AFM-G2 described in the present invention has 50% inhibiting concentration $IC_{50}$ to aflatoxin M1 of 0.208 ng/mL, and its cross reaction rates with aflatoxin B1, B2, G1, G2 are 9.43%, 5.93%, 4.87% and 6.17%, respectively. The prepared aflatoxin M1 nanobody immunoaffinity column has a column capacity of 500-600 ng, and has an average spiked recovery rate of 84-100 wt % to aflatoxin M1.

(2) The aflatoxin M1 nanobody immunoaffinity column of the present invention has advantages such as good stability, tolerance to high temperature, tolerance to acids and bases, and tolerance to organic reagents and the like, and has a long shelf life, thus can be used repeatedly for many times and can be used for purifying and concentrating the extracting solution of the sample before loading the sample to a machine for detection.

(3) The aflatoxin M1 nanobody of the present invention is obtained via a genetic engineering means, having the advantages such as low cost and convenience for preparation. Therefore the aflatoxin M1 nanobody immunoaffinity column prepared from the nanobody is more advantageous than conventional antibody immunoaffinity columns.

DETAINED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprising", "including", "carrying", "having", "containing", "involving", and the like are to be understood to be open-ended, i.e., to mean including but not limited to.

Example 1

Construction of an Aflatoxin Nanobody Gene Library and Preparation of Nanobodies 1. Immunization of Animals One male alpaca of 2 years old was purchased and immunized with the aflatoxin M1 complete antigen ($AFM_1$-BSA, Sigma-Aldrich Corporation). 200 μg of aflatoxin M1 complete antigen was emulsified with Freund's incomplete adjuvant, and subcutaneously injected to the alpaca at multiple points. The alpaca was immunized in an interval of 2 weeks. Blood was sampled intravenously from the alpaca 7-10 days after each immunization, and serum titer was determined using an indirect ELISA method. After selecting an immunization with the highest titer, 10 mL of blood was sampled for extracting the total RNA.

2. Construction of a cDNA Library (1) Extraction of the total RNA: after selecting an immunization with the highest serum titer in the alpaca, and 7-10 days after immunization, 10 mL of blood was sampled intravenously from the alpaca for extracting total RNA: the total RNA was extracted from the blood of the alpaca using LeukoLOCK Total RNA Isolation System of Life Technologies.

(2) Synthesis of cDNA: using the total RNA obtained in step 1 as the template and oligo $(dT)_{15}$ as the primer, and performing reverse transcription according to the reverse transcriptase instruction of Promega Inc. to synthesize the first strand of cDNA to obtain the cDNA library.

3. Construction of the Aflatoxin Nanobody Gene Library (1) using the cDNA obtained in step 2 as the template, and R1, F or R2, F as primers, performing PCR amplification to obtain the variable region genes of the heavy chains of the antibodies of the alpaca, i.e., VHH genes: taking cDNA 2 µl, 10×PCR Buffer 5 µl, $MgSO_4$ (50 mM) 2 µl, dNTP (10 mmol/L) 1 µl, F primers (10 µmol/L) 1 µl, R1 (or R2) primers (10 µmol/L) 1 µl, DNAase 0.1 µl, sterile purified water 37.9 µl, in total volume of 50 µl, vortexing uniformly, centrifuging briefly, performing PCR amplification reaction with the reaction conditions of: 94° C. denaturing for 2 min; followed by 30 cycles of 94° C. denaturing for 30 s, 55° C. annealing for 30 s, and 68° C. elongation for 1 min; and 68° C. elongation for 5 min. The primers are:

```
R1:
                                            (SEQ ID NO: 9)
5'-CGG CGC ACC TGC GGC CGCATGGGGGTCTTCGCT
GTGGTGCG-3';

R2:
                                           (SEQ ID NO: 10)
5'-CGG CGC ACC TGC GGC CGCGTCTTGTGGTTTTGG
TGTCTTGGG-3';
and F:
                                           (SEQ ID NO: 11)
5'-TCCTTTCTATGCGGCCCAGCCGGCCATGGCCCCAGKTG
CAGCTCGTGGAGTC-3',
``` in which the primer sequences indicated by the underlined parts are sites homologous to the vector pCANTAB 5E (his); 4 PCR amplification reactions were performed using R1, F as primers, and 6 PCR amplification reactions were performed using R2, F as primers. PCR products were separated by 0.7% agarose gel electrophoresis, and DNA fragments of 450 bp size were recovered using purification kit.

(2) Construction of the pCANTAB 5E (his) vector: using pCANTAB5E vector plasmid as the template, p5E SfiI-F: 5'-ATGCGGCCCAGCCGGCC-3'(Sfi I, SEQ ID NO:12) as the upstream primer and p5E N-P-H-R: 5'-GATCGGGC-CCTGTGGTGGTGGTGGTGGTGTGCGGCCGC-CCGTTTTC-3' (SEQ ID NO:13) as the downstream primer, PCR amplifying a DNA fragment between the Sfi I and NotI on the pCANTAB5E vector plasmid, to obtain p5E-his fragments. Then, firstly subjecting the p5E-his fragments to single enzyme digestion using SfiI followed by single enzyme digestion using PspoMI to obtain p5E-his (SfiI/PspoMI) cohesive termini, subjecting the pCANTAB5E vector plasmid to single enzyme digestion using SfiI followed by single enzyme digestion using Not I to obtain p5E (SfiI/NotI) cohesive termini. Finally ligating the p5E-his (SfiI/PspoMI) cohesive termini to the p5E (SfiI/NotI) cohesive termini to obtain the pCANTAB 5E (his) vector containing hexahistidine tag.

(3) Double Enzyme Digestion Treatment of pCANTAB 5 E (his):

Sfi I single enzyme digestion: reaction solution was prepared according to the following system:

| | |
|---|---|
| pCANTAB 5 E (his) vector | 30 µl |
| Sfi I | 1 µl |
| 10 × M Buffer | 10 µl |
| ddH$_2$O added up to the total system | 100 µl |

50° C. water bath for 2 h, followed by recovering using agarose gel DNA purification kit.

Not I enzyme digestion: reaction solution was prepared according to the following system:

| | |
|---|---|
| pCANTAB 5 E (his) product recovered via Sfi I single enzyme digestion | 30 µl |
| Not I | 1 µl |
| 10 × H Buffer | 10 µl |
| ddH$_2$O added up to the total system | 100 µl |

37° C. water bath for 4 h, followed by recovering using agarose gel DNA purification kit.

(4) Ligation of the VHH gene to the pCANTAB 5 E (his) vector treated via double enzyme digestion In-fusion ligation was performed according to the following system:

| | |
|---|---|
| pCANTAB 5 E (his) vector treated with Sfi I/Not I double enzyme digestion | 120 ng |
| VHH gene | 40 ng |
| 5 × In-Fusion buffer | 2 µl |
| In-Fusion Enzyme | 1 µl |
| ddH$_2$O added up to the total system | 10 µl |

37° C. water bath for 15 min followed by placing into 50° C. water bath for 15 min, then immediately placing onto ice and keeping for 5 min, adding 40 µl TE buffer, recovering using agarose gel DNA purification kit, and storing at −20° C. for use.

(5) Electrotransformation of the Ligated Product

5 µl of the above ligated product was taken and added to 50 µl electrotransformation-competent cells of *E. coli* TG1 and mixed uniformly, followed by adding to prechilled 0.1 cm electrotransformation cuvette (Bio-RAD), placing on ice and keeping for 10 min, then placing on Bio-rad electrotransformer for performing electrotransformation under the electrotransformation conditions of 1.8 kV, 200Ω, and 25 µF, followed by immediately adding 1 mL 2YT liquid medium to the electrotransformation cuvette, pipetting up and down, transferring to a 15 mL sterilized clean shake tube, and reviving cells at 37° C. under slow shaking for 1 h. 2 µl of bacterial culture was taken and subjected to double dilution, followed by spreading onto LB-ampicillin plates, inverting, and culturing at 37° C. overnight, and calculating the library capacity by counting the number of colonies in the next day.

(6) Rescue of aflatoxin nanobody gene library: the above-mentioned electrotransformation was performed ten times in total, the revived bacterial culture was entirely transferred to 200 mL SB medium and shaken at 37° C. under 250 rpm until $OD_{600}$ value was 0.5, and then 1 mL helper phage M13KO7 with 1×10$^{12}$ pfu was added, followed by standing at 37° C. for 1 h, continuing to shake for 2 h, adding kanamycin to reach a final concentration of 70 μg/mL and shaking overnight. The next day, the overnight bacteria culture were centrifuged at 4° C. under 10,000 rpm for 15 min, the supernatant was transferred to a sterile centrifuge bottle, ¼ volume of 5×PEG/NaCl was added, followed by standing on ice for 2 h, centrifuging at 4° C. at 12,000 rpm for 20 min, and dissolving the pellets in 10 mL sterile resuspension solution (PBS buffer containing 1× protease inhibitor, 0.02% NaN$_3$ and 0.5% BSA) to obtain the phage-rescued aflatoxin nanobody gene library.

4. Panning of Aflatoxin M1 Nanobodies

ELISA plates were coated with AFM$_1$-BSA (1 μg/well) and 3% of BSA-PBS solution (used as the negative control) respectively at 4° C. overnight. In the next day, the coating solutions were poured off, the plates were washed with PBST for 3 times, and blocked with 3% skimmed milk powder for 1 h. The plates were washed with PBST for 3 times, 50 μl of the above-mentioned rescued aflatoxin nanobody gene library was added to the wells coated with AFM$_1$-BSA, and incubated at 37° C. for 1 h. The plates were washed with PBST for 10 times, 100 μl 100 ng/mL AFM$_1$ solution was added to each well, and elution is performed via shaking at room temperature (20° C.-30° C.) for 30 min. The eluate was transferred to the wells coated with 3% BSA-PBS solution and incubated at 37° C. for 1 h (removing non-specific adsorption). After incubation, the supernatant was taken to infect 2 mL of TG1 bacterial culture that has grown to the logarithmic phase, the infection was allowed at 37° C. for 20 min, followed by respectively taking 1 μl and 10 μl infected bacterial culture and spreading onto LB-ampicillin plates. The LB-ampicillin plates were sitting in an incubator at 37° C. overnight, and the phage titer in the eluate was determined by counting the number of the colonies on the plates in the next day. Additionally, the remaining above-mentioned TG1 bacterial culture after infection was transferred to 6 mL SB medium, 1.5 μl 100 mg/mL ampicillin was added, and the mixture was shaken at 37° C. for 1 h. Then supplementing ampicillin to reach a final concentration of 50 μg/mL and continuing to shake for 1 h, adding 1 mL of helper phage M13KO7 (1×10$^{12}$ pfu/mL), standing at 37° C. for 30 min, transferring to 100 mL SB medium, supplementing 46 μl ampicillin (100 mg/mL), continuing to shake for 2 h, adding kanamycin to reach a final concentration of 70 μg/mL, and shaking at 37° C. overnight. The next day, the bacterial culture was centrifuged under 10,000 rpm at 4° C. for 15 min, followed by transferring supernatant, adding ¼ volume of PEG/NaCl solution, incubating on ice for 2 h, centrifuging under 12,000 rpm at 4° C. for 20 min, and dissolving the pellets with 1% BSA-PBS solution to obtain the amplified product of the first round of panning, which was used for the next round of panning. In the subsequent several rounds of panning, the concentrations of the coating antigen AFM$_1$-BSA were 0.5 μg/well, 0.1 μg/well, 0.05 μg/well, respectively, and the eluents were AFM$_1$ solutions of 500 ng/mL, 100 ng/mL, 50 ng/mL, respectively.

5. Identification of Positive Clones

After 4 rounds of panning, 2 μl of eluate was taken and subjected to double dilution, followed by infecting TG1 bacterial culture that has grown to the logarithmic phase. The infected TG1 bacterial culture was spread onto LB-ampicillin plates. The plates were placed invertedly, and incubated at 37° C. overnight. The next day, 30 clones were randomly picked out, and each of the clones was transferred to 3 mL SB-ampicillin culture medium, and cultured at 37° C. for 6-8 h under shaking until OD$_{600}$ was about 0.6. The culture medium was added with 30 μl helper phage M13KO7 (1×10$^{12}$ pfu/mL), sit at 37° C. for 30 min, shaken for 2 h, added with kanamycin to reach a final concentration of 70 μg/mL, cultured under shaken overnight, and centrifuged in the next day under 10,000 rpm at 4° C. for 15 min to obtain the supernatant of the bacterial culture.

AFM$_1$-BSA was prepared using coating solution to reach a final concentration of 0.2 μg/ml. The prepared 0.2 μg/ml AFM$_1$-BSA was used to coat 96-well ELISA plate, with 100 μl in each well. Meanwhile another ELISA plate was taken, 32 wells of which were coated with 3% BSA, and the plate was coated at 4° C. overnight. In the next day, the coating solution was pouring off, the plates were washed with PBST for 3 times, and then blocked with 3% skimmed milk powder-PBS for 1 h. AFM$_1$ standard stock solution was taken and prepared into 100 ng/mL and 0 ng/mL working solutions using 10% methanol/PBS, and respectively added to the wells coated with AFM$_1$-BSA antigens, and then 50 μl of the above-mentioned supernatant of bacterial culture was added to each well. Each concentration of the working solutions was repeated for 3 times. 10% methanol/PBS and 50 μl of the above-mentioned supernatant of bacterial culture were added to the wells coated with BSA as the control, the plates were gently shaken and mixed uniformly, and placed at 37° C. incubator to allow reaction for 1 h. The plates were washed with PBST 10 times, and 100 μl of HRP/ANTI-M13 diluted with PBS in a ratio of 1:5000 was added to each well, and the plates were incubated at 37° C. for 1 h. The plates were washed with PBST 6 times, 100 μl freshly prepared TMB substrate solution was added to each well, and the plates were incubated at 37° C. for 15 min. 50 μl 2 mol/L H$_2$SO$_4$ was added to each well to terminate the reaction, and OD$_{450}$ values were measured using a plate reader. The positive phage clones were those did not adsorb BSA, while adsorbed AFM$_1$-BSA, and had competition upon the addition of aflatoxin. The wells having both relatively high absorbance value and sensitivity were chosen, so as to obtain the phage-displayed aflatoxin M1 nanobody 2014AFM-G2.

The antibody specificity of aflatoxin M1 nanobody 2014AFM-G2, described particularly using the cross reaction rate, was determined using indirect competitive ELISA method. The test method was as follows: diluting five different standard stock solutions of AFM$_1$, AFB$_1$, AFB$_2$, AFG$_1$ and AFG$_2$ in gradient to ten different working concentrations using 10% methanol/PBS, determining using the indirect competitive ELISA method under the same conditions, sequentially drawing five competitive ELISA curves for the five aflatoxins, calculating the standard concentrations when the inhibition rate was 50%, which were represented by IC$_{50}$, and calculating cross reaction rates according to the following calculation formula: cross reaction rate (%)=(AFM$_1$ IC$_{50}$/analogue IC$_{50}$)×100%, where the analogue was AFB$_1$, AFB$_2$, AFG$_1$ or AFG$_2$. The 50% inhibiting concentration IC$_{50}$ of aflatoxin M1 nanobody 2014AFM-G2 to aflatoxin M1 was 0.208 ng/mL, and the cross reaction rates with aflatoxin B1, B2, G1, and G2 were 9.43%, 5.93%, 4.87% and 6.17%, respectively. Therefore, the aflatoxin M1 nanobody 2014AFM-G2 was a specific nanobody against aflatoxin M1. It can be seen from tolerance tests that as compared with conventional murine source antibodies and rabbit source antibodies, the tolerance capability of aflatoxin nanobody 2014AFM-G2 to organic solvents was improved by 35%, and the tolerance to high temperature thereof was improved by 45%. Therefore, this nanobody can effectively reduce the interference of other ingredients such as the organic solvents in the extracting solution of the sample during detection, thus improving the detection sensitivity.

Meanwhile, the screened clonal bacterial culture containing aflatoxin M1 nanobody 2014AFM-G2 was sent to Shanghai Sunny Biotechnology Co., Ltd. to conduct sequencing analysis. The sequencing primer was phage vector universal primer R1: 5'-CCA TGA TTA CGC CAA GCT TTG GAG CC-3' (SE ID NO:14). The obtained amino acid sequence of the aflatoxin M1 nanobody 2014AFM-G2 was shown in SEQ ID NO:7, the encoding gene sequence thereof was shown in SEQ ID NO:8, where the amino acid sequences of the three complementary determining regions were: the amino acid sequence of CDR1 as shown in SEQ ID NO:1, the amino acid sequence of CDR2 as shown in SEQ ID NO:2, the amino acid sequence of CDR3 as shown in SEQ ID NO:3, respectively; the encoding gene sequences of the three complementary determining regions were: the encoding gene sequence of CDR1 as shown in SEQ ID NO:4, the encoding gene sequence of CDR2 as shown in SEQ ID NO:5, and the encoding gene sequence of CDR3 as shown in SEQ ID NO:6, respectively.

6. Preparation and Purification of Aflatoxin M1 Nanobody 2014AFM-G2

(1) TG1 bacterial culture capable of secreting aflatoxin M1 nanobody 2014AFM-G2 was obtained, DNA miniextraction kit of Qiagen was used to extract plasmids. The extracted plasmids were transformed to HB2151 competent cells, and the transformed competent cells were spread onto LB-ampicillin plates.

(2) HB2151 colonies containing aflatoxin M1 nanobody 2014AFM-G2 plasmids were picked out and inoculated onto 100 mL SB-ampicillin liquid culture medium. The inoculated culture medium was cultured under 250 rpm at 37° C. until OD600=0.5-0.8, and 200 µl 0.5 M IPTG solution was added to the culture medium to induce overnight.

(3) The cultured medium after induction was centrifuged at 4° C. under 10,000 rpm for 15 min. The supernatant was removed carefully in a sterile operation platform, and the bacterial cell pellets were subjected to soluble protein extraction using an osmotic shock method to obtain the proteins from the supernatant. The proteins from the supernatant were filtered using a 0.22 µm filter membrane, and dialyzed in an equilibrium buffer (50 mM phosphate, 300 mM sodium chloride, 20 mM imidazole, pH7.4) overnight.

(4) His60 nickel column (Clontech Technology) was used to purify antibodies. Firstly, the nickel column was rinsed with 10 folds the column volume of an equilibrium buffer. The proteins of the supernatant dialyzed in step (3) were loaded to His60 nickel column (Clontech Technology) for antibody purification. Then the column was washed with 10 folds the column volume of a rinsing buffer (50 mM phosphate, 300 mM sodium chloride, 40 mM imidazole, pH7.4). Finally, the antibody 2014AFM-G2 was eluted with 10 folds the column volume of an elution buffer (50 mM phosphate, 300 mM sodium chloride, 300 mM imidazole, pH7.4). The eluates were collected and put into a dialysis bag, dialyzed and concentrated using 0.01 M, pH7.4 phosphate buffer for 2-3 days, fractionized and stored at −20° C. for use.

Example 2

Preparation of the Aflatoxin M1 Nanobody Immunoaffinity Adsorbent and Immunoaffinity Column In this example, the immunoaffinity adsorbent included a solid phase carrier (silica gel microspheres) and aflatoxin M1 nanobody 2014AFM-G2 coupled to the solid phase carrier. The preparation method of the immunoaffinity adsorbent is as follows:

weighing 1 g acrylamide silica gel microspheres, placing into a conical flask, and alternately rinsing the microspheres with purified water and pH6.0 phosphate buffer; measuring 5 mL, pH6.0 phosphate buffer to dissolve the microspheres to give a microsphere solution, transferring the microsphere solution to a stirring mug, starting a stirrer to make all of the microspheres suspended, using 1 mL, pH6.0 phosphate buffer to dissolve 2 mg aflatoxin M1 nanobody 2014AFM-G2, then adding dropwise to the above-mentioned microsphere solution, weighing 70 mg 1-ethyl-3-(3-dimethylaminopropyl)carbodiimide hydrochloride (EDC), rapidly introducing into the stirring mug, and stirring at 4° C. to allow reaction for 18-22 h to obtain the aflatoxin M1 nanobody immunoaffinity adsorbent.

Preparation of the aflatoxin M1 nanobody immunoaffinity column: filling the immunoaffinity adsorbent (0.2 mL) prepared as described above to a solid-phase extraction tube with, adding 0.01 M, pH6.0 phosphate buffer and allowing precipitation to naturally occur, then washing with 0.01 M, pH6.0 phosphate buffer, storing in 0.01 M, pH6.0 phosphate buffer containing 0.02 wt % sodium azide to obtain the aflatoxin M1 nanobody immunoaffinity column, and storing at 4° C. for use.

Example 3

Preparation of the Aflatoxin M1 Nanobody Immunoaffinity Adsorbent and Immunoaffinity Column In this example, the immunoaffinity adsorbent included a solid phase carrier (agarose) and aflatoxin M1 nanobody 2014AFM-G2 coupled to the solid phase carrier. The preparation method of the immunoaffinity adsorbent is as follows:

weighing 0.3 g agarose, placing into a conical flask, repeatedly rinsing with 1 mM HCl solution for more than 15 min, dissolving agarose in 5 mL coupling buffer (0.1 M NaCO3 plus 0.5 M NaCl, pH8.3), then adding 0.6 mg aflatoxin M1 nanobody 2014AFM-G2, stirring at room temperature under the speed of 150 rpm to allow reaction for 1 h to obtain an agarose gel solution, transferring the agarose gel solution to a separatory funnel, allowing the uncoupled antibody-containing solution to flow out, then rinsing agarose gel with a coupling buffer having a volume of 5 folds that of the agarose gel solution, then adding a blocking buffer (0.1 M Tris-HCl buffer, pH8.0) having a volume of 2 folds of that of the agarose gel solution to allow reaction at room temperature for 2 h, and then alternately rinsing the gel with a high pH buffer (0.1 M Tris-HCl buffer, pH8.0) and a low pH buffer (0.1 M Tris-HCl buffer, pH4.0) for three times to obtain the aflatoxin M1 nanobody immunoaffinity adsorbent.

Preparation of the aflatoxin M1 nanobody immunoaffinity column: filling immunoaffinity adsorbent (0.2 mL) prepared as described above to a solid-phase extraction tube, adding 0.01 M, pH6.0 phosphate buffer and allowing precipitation to naturally occur, then washing with 0.01 M, pH6.0 phosphate buffer, storing in 0.01 M, pH6.0 phosphate buffer containing 0.02 wt % sodium azide to obtain the aflatoxin M1 nanobody immunoaffinity column, and storing at 4° C. for use.

Example 4

Determination of Capacity of the Aflatoxin M1 Nanobody Immunoaffinity Column The immunoaffinity column obtained in example 2 or example 3 was rinsed with 10 mL of purified water. 10 mL aflatoxin M1 standard solution (with a concentration of 100 ng/mL, the content of aflatoxin M1 being 1 mg in total) dissolved in 10% methanol/PBS was loaded to the column. The column was rinsed with 10 mL purified water to remove the unbound aflatoxin M1. Finally the column was eluted with 5 mL methanol solution, and collected in fractions of 1 mL per tube. The content of aflatoxin M1 in the eluate was detected using liquid phase chromatography. The result showed that the column capacity of the aflatoxin M1 nanobody immunoaffinity column was 500-600 ng. After repeatedly used for 5 times, the column capacity of the immunoaffinity column was measured, which still reached 480 ng. The result indicated that the immunoaffinity column can be used repeatedly for many times. Meanwhile, the result of cross reaction determination showed that the aflatoxin M1 nanobody immunoaffinity column described in the present invention can specifically bind aflatoxin M1, but not bind other fungal toxins such as zearalenone, vomitoxin, ochratoxin.

Example 5

Determination of Spiked Recovery Rate of the Aflatoxin M1 Nanobody Immunoaffinity Column 10 mL of milk (cow) product was filled to a 50 mL centrifuge tube, and centrifuged under 3,500 g at 4° C. for 10 min. The milk fat portion of the upper layer was removed, and the middle portion (that is, a milk sample) was kept. 10 g milk powder was weighed accurately and dissolve in 50° C. preheated purified water, and added up to 100 mL. The 100 mL milk powder solution was centrifuged under 3,500 g at 4° C. for 10 min. The milk fat portion of the upper layer was removed, and the middle portion (that is, a milk powder sample) was kept. AFM1 standards were added to the milk sample and the milk powder sample respectively to reach concentrations of 50, 100, and 500 µg/mL. Each sample containing AFM1 standard was extracted with 15 mL 70% methanol solution (containing 4% NaCl) under ultrasonication, at 50° C. for 10 min. The extraction solution was filtered with a filter paper. 4 mL filtrate was taken, and added with 2 mL petroleum ether. The mixture of the filtrate and the petroleum ether was vortexed to mix uniformly, and sit to allow layering. 3 mL lower layer was taken, and added with 8 mL purified water, and filtered with 0.45 µm organic membrane to obtain the filtrate. The prepared immunoaffinity column was rinsed with 10 mL purified water, added with 8 mL the above filtrate, and rinsed with 10 mL purified water. After the ringing liquid was drain completely, the column was eluted with 1 mL methanol. The eluate was collected for loading to a machine for detection. The detection results showed that the average recovery rate of aflatoxin M1 of the milk sample was 97.3 wt % and the average recovery rate of aflatoxin M1 of the milk powder sample was 98 wt %.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An aflatoxin M1 nanobody immunosorbent, comprising:
a solid phase carrier; and
an aflatoxin nanobody coupled to the solid phase carrier, wherein the aflatoxin nanobody consists of aflatoxin M1 nanobody 2014AFM-G2,
wherein the aflatoxin M1 nanobody 2014AFM-G2 comprises the amino acid sequence of SEQ ID NO:7, encoded by the nucleic acid sequence of SEQ ID NO:8; wherein the aflatoxin M1 nanobody 2014AFM-G2 comprises further three complementary determining regions of: CDR1 consisting of amino acid sequence of SEQ ID NO: 1; CDR2 consisting of amino acid sequence of SEQ ID NO:2; and CDR3 consisting of amino acid sequence of SEQ ID NO:3; wherein the CDR1 is encoded by the nucleic acid sequence of SEQ ID NO:4; the CDR2 is encoded by the nucleic acid sequence of SEQ ID NO:5; and the CDR3 is encoded by the nucleic acid sequence of SEQ ID NO:6; and wherein the aflatoxin M1 nanobody immunosorbent specifically binds aflatoxin M1.

2. The aflatoxin M1 nanobody immunosorbent according to claim 1, wherein the solid phase carrier is an agarose gel or silica gel microspheres.

3. A preparation method of the aflatoxin M1 nanobody immunosorbent of claim 1,
wherein when silica gel microspheres are chosen as the solid phase carrier, the preparation method of the aflatoxin M1 nanobody immunosorbent comprises: weighing 1-5 g silica gel microspheres, alternately rinsing with purified water and pH6.0 phosphate buffer, weighing 5-25 mL, pH6.0 phosphate buffer to dissolve the silica gel microspheres, and stirring to make all of the silica gel microspheres suspended to obtain a suspension of silica gel microspheres; dissolving 2-10 mg aflatoxin M1 nanobody 2014AFM-G2 in 1-5 mL, pH6.0 phosphate buffer, and then adding dropwise to the suspension of silica gel microspheres; and finally weighing 70-350 mg carbodiimide, rapidly adding to the suspension of silica gel microspheres, and allowing reaction under stirring at 4° C. for 18-22 h to obtain the aflatoxin M1 nanobody immunosorbent using silica gel microspheres as the solid phase carrier; and when agarose gel is chosen as the solid phase carrier, the preparation method of the aflatoxin M1 nanobody immunosorbent comprises: weighing 0.3-1 g agarose, repeatedly rinsing with 1 mM HCl solution, dissolving agarose in 5-15 mL coupling buffer, then adding 0.6-2 mg aflatoxin M1 nanobody 2014AFM-G2, stirring at room temperature for reaction for 1-2 h to obtain an agarose gel solution, filtering the antibody solution in the agarose gel solution which is not coupled with the agarose gel, rinsing the agarose gel with a coupling buffer, then adding 0.1 M Tris-HCl buffer having pH8.0, allowing reaction at room temperature for 2 h, and then alternately rinsing the agarose gel with 0.1 M Tris-HCl buffer having pH8.0 and 0.1 M Tris-HCl buffer having pH4.0 to obtain the aflatoxin M1 nanobody immunoaffinity adsorbent using the agarose gel as the solid phase carrier, wherein said coupling buffer is 0.1 M NaCO3 plus 0.5 M NaCl having pH8.3.

4. An aflatoxin M1 nanobody immunoaffinity column loaded with the aflatoxin M1 nanobody immunosorbent according to claim 1.

5. A preparation method of the aflatoxin M1 nanobody immunoaffinity column of claim 4, comprising: filling a solid-phase extraction tube with the aflatoxin M1 nanobody immunosorbent, adding 0.01 M, pH6.0 phosphate buffer and allowing precipitation to naturally occur, washing with 0.01 M, pH6.0 phosphate buffer, and storing in 0.01 M, pH6.0 phosphate buffer containing 0.02 wt % sodium azide to obtain the aflatoxin M1 nanobody immunoaffinity column.

6. A method for purification and concentration of aflatoxin M1 comprised in an extracting solution of a sample using the aflatoxin M1 nanobody immunoaffinity column according to claim 4, the method comprising:
firstly rinsing the prepared aflatoxin M1 nanobody immunoaffinity column with purified water,
then adding the extracting solution of the sample,
rinsing with purified water wherein after the liquid drain completely, eluting with methanol; and
collecting the eluate, wherein the eluate is the purified and concentrated extracting solution of the sample, which can be used directly for loading to a machine for detection.

* * * * *

SEQUENCE LISTING

```
<160> NUMBER OF SEQ ID NOS: 14

<210> SEQ ID NO 1
<211> LENGTH: 8
<212> TYPE: PRT
<213> ORGANISM: Vicugna vicugna

<400> SEQUENCE: 1

Gly Arg Thr Phe Ser Ser Tyr Ala
1               5

<210> SEQ ID NO 2
<211> LENGTH: 8
<212> TYPE: PRT
<213> ORGANISM: Vicugna vicugna

<400> SEQUENCE: 2

Val Asn Trp Ser Gly Arg Arg Thr
1               5

<210> SEQ ID NO 3
<211> LENGTH: 14
<212> TYPE: PRT
```

-continued

<213> ORGANISM: Vicugna vicugna

<400> SEQUENCE: 3

Ala Ala Gly Lys Asp Gly Ser Tyr Tyr Gly Ala Pro Asp Tyr
1               5                   10

<210> SEQ ID NO 4
<211> LENGTH: 24
<212> TYPE: DNA
<213> ORGANISM: Vicugna vicugna

<400> SEQUENCE: 4
ggacgcacct tcagtagcta tgcc                                          24

<210> SEQ ID NO 5
<211> LENGTH: 24
<212> TYPE: DNA
<213> ORGANISM: Vicugna vicugna

<400> SEQUENCE: 5
gttaactgga gtggtcgccg caca                                          24

<210> SEQ ID NO 6
<211> LENGTH: 42
<212> TYPE: DNA
<213> ORGANISM: Vicugna vicugna

<400> SEQUENCE: 6
gcagccggga aggatggtag ttactatggc gctcctgact ac                      42

<210> SEQ ID NO 7
<211> LENGTH: 130
<212> TYPE: PRT
<213> ORGANISM: Vicugna vicugna

<400> SEQUENCE: 7

Gln Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Val Val Asn Trp Ser Gly Arg Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Asn Cys
                85                  90                  95

Ala Ala Gly Lys Asp Gly Ser Tyr Tyr Gly Ala Pro Asp Tyr Trp Gly
            100                 105                 110

Gln Gly Thr Gln Val Thr Val Ser Ser Glu Pro Lys Thr Pro Lys Pro
        115                 120                 125

Gln Asp
    130

<210> SEQ ID NO 8
<211> LENGTH: 390
<212> TYPE: DNA
<213> ORGANISM: Vicugna vicugna

<400> SEQUENCE: 8

```
cagttgcagc tcgtggagtc tgggggagga ttggtgcagg ctgggggctc tctgagactc    60
tcctgtgcag cctctggacg caccttcagt agctatgcca tgggctggtt ccgccaggct   120
ccagggaagg agcgtgagtt tgtagcagtc gttaactgga gtggtcgccg cacatactat   180
gcagactccg tgaagggccg attcaccatc tccagagaca cgccaagaa cacggtgtat   240 ctgcaaatga acagcctgaa acctgaggac acggctgttt ataactgtgc agccgggaag   300
gatggtagtt actatggcgc tcctgactac tgggggcagg ggacccaggt caccgtctcc   360
tcagaaccca agacaccaaa accacaagac                                    390

<210> SEQ ID NO 9
<211> LENGTH: 41
<212> TYPE: DNA
<213> ORGANISM: Artificial Sequence
<220> FEATURE:
<223> OTHER INFORMATION: Primer

<400> SEQUENCE: 9
cggcgcacct gcggccgcat gggggtcttc gctgtggtgc g                        41

<210> SEQ ID NO 10
<211> LENGTH: 42
<212> TYPE: DNA
<213> ORGANISM: Artificial Sequence
<220> FEATURE:
<223> OTHER INFORMATION: Primer

<400> SEQUENCE: 10
cggcgcacct gcggccgcgt cttgtggttt tggtgtcttg gg                       42

<210> SEQ ID NO 11
<211> LENGTH: 52
<212> TYPE: DNA
<213> ORGANISM: Artificial Sequence
<220> FEATURE:
<223> OTHER INFORMATION: Primer

<400> SEQUENCE: 11
tcctttctat gcggcccagc cggccatggc cccagktgca gctcgtggag tc             52

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
atgcggccca gccggcc                                                   17

<210> SEQ ID NO 13
<211> LENGTH: 46
<212> TYPE: DNA
<213> ORGANISM: Artificial Sequence
<220> FEATURE:
<223> OTHER INFORMATION: Primer

<400> SEQUENCE: 13
gatcgggccc tgtggtggtg gtggtggtgt gcggccgccc gttttc                    46

<210> SEQ ID NO 14
<211> LENGTH: 26
<212> TYPE: DNA
```

```
<213> ORGANISM: Artificial Sequence
<220> FEATURE:
<223> OTHER INFORMATION: Primer

<400> SEQUENCE: 14
ccatgattac gccaagcttt ggagcc                                            26
```